(12) United States Patent
Pedersen et al.

(10) Patent No.: US 9,284,651 B2
(45) Date of Patent: Mar. 15, 2016

(54) APPARATUS FOR PRODUCTION OF HIGH PURITY CARBON MONOXIDE

(71) Applicants: Friis Claus Pedersen, Vanløse (DK); Bøgild John Hansen, Copenhagen Ø (DK); Thomas Rostrup-Nielsen, Holte (DK); Jens Ulrik Nielsen, Søborg (DK); Henrik Olsson, Malmö (SE); Kim Hedegaard Andersen, Kgs. Lyngby (DK)

(72) Inventors: Friis Claus Pedersen, Vanløse (DK); Bøgild John Hansen, Copenhagen Ø (DK); Thomas Rostrup-Nielsen, Holte (DK); Jens Ulrik Nielsen, Søborg (DK); Henrik Olsson, Malmö (SE); Kim Hedegaard Andersen, Kgs. Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/382,948

(22) PCT Filed: Feb. 26, 2013

(86) PCT No.: PCT/EP2013/053780
§ 371 (c)(1),
(2) Date: Sep. 4, 2014

(87) PCT Pub. No.: WO2013/131778
PCT Pub. Date: Sep. 12, 2013

(65) Prior Publication Data
US 2015/0038741 A1 Feb. 5, 2015

(30) Foreign Application Priority Data
Mar. 5, 2012 (WO) .............. PCT/EP2012/000976

(51) Int. Cl.
| | |
|---|---|
| C25B 1/00 | (2006.01) |
| C25B 9/18 | (2006.01) |
| C25B 3/04 | (2006.01) |
| C25B 1/02 | (2006.01) |
| C07C 51/10 | (2006.01) |

(52) U.S. Cl.
CPC . *C25B 1/00* (2013.01); *C07C 51/10* (2013.01); *C25B 1/02* (2013.01); *C25B 9/18* (2013.01)

(58) Field of Classification Search
CPC ............................... C07C 51/10; C25B 1/00
USPC ................. 562/607; 204/278, 230.2; 205/555
See application file for complete search history.

(56) References Cited

U.S. PATENT DOCUMENTS

| | | |
|---|---|---|
| 6,054,025 A | 4/2000 | Moriguchi et al. |
| 6,428,678 B1 | 8/2002 | Rennebeck |
| 2009/0263681 A1 | 10/2009 | Atreya et al. |
| 2011/0155583 A1 | 6/2011 | Li |
| 2011/0253551 A1* | 10/2011 | Lane .................... B01D 53/326 205/555 |
| 2012/0018493 A1 | 1/2012 | Baffie et al. |

FOREIGN PATENT DOCUMENTS

CN        1219609 A        6/1999

* cited by examiner

*Primary Examiner* — Yong Chu
(74) *Attorney, Agent, or Firm* — Dickstein Shapiro LLP

(57) ABSTRACT

A device and a process for producing high purity CO by electrolysis of CO2 in a Solid Oxide Electrolysis Cell stack and a gas separation unit, also the gas separation unit may be a Solid Oxide Electrolysis Cell stack.

7 Claims, 6 Drawing Sheets

Figure 1:
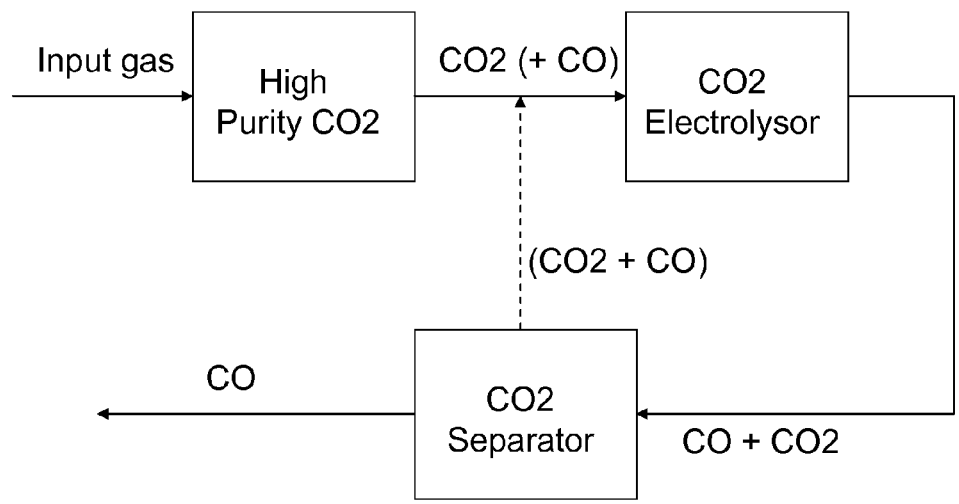

Leakage
------▶

APPARATUS FOR PRODUCTION OF HIGH PURITY CARBON MONOXIDE

The present invention concerns an apparatus for production of high purity carbon monoxide, CO, based on electrolysis of carbon dioxide, CO2 in combination with a high purity CO2 feedstock and gas cleaning operation at temperatures above −100° C. In particular, Solid Oxide Electrolysis Cells, SOEC, are used for the electrolysing.

The proposed invention relates to the production of CO of high purity where the purification relies on simple, low cost purification techniques that do not involve cryogenic techniques.

Traditionally CO is produced on commercial scale by reforming hydro-carbons, e.g.:

$$CH4+H2O \rightarrow CO+4H2$$

or $$4CH4+O2+2H2O \rightarrow 10H2+4CO$$

The product gas (CO+H2) is then purified to high purity CO (typically>99%) in different steps, for instance including a final cryogenic state to separate H2 from the CO and to remove possible impurities of N2 and Ar.

CO boils at −205° C., H2 at −252.87° C. and this cryogenic process is therefore very expensive and has to be carried out at large central facilities. This leads to long distribution paths between the CO production site and the end user and with CO being a poisonous gas, subject to strict safety requirements during handling, transportation and storage, this add significantly to the cost. Consequently, the price for smaller quantities (e.g. <100 Nm3/h) of high purity CO is 5-10 times higher than the price of the H2 produced in the same reforming process.

It is an object of the present invention to provide an apparatus and a method for the production of CO which solves the above mentioned problems.

More specifically it is an object of the present invention to provide an SOEC apparatus and method to produce CO at a lower cost than the presently known techniques.

It is a further object of the present invention to provide an SOEC apparatus and method to produce CO at a low cost and at a high purity without the use of cryogenic techniques.

The invention relates to a CO production and purification method which is based on CO2 electrolysis in combination with simple and in-expensive 'room temperature' gas cleaning and gas separation methods. This invention makes it technically and economically feasible to produce high purity CO in small quantities, for example at the consumption site or at local distribution centres.

CO2 electrolysis is less known than water electrolysis as fewer techniques are available for CO2 electrolysis. One technology which is very efficient for CO2 electrolysis is Solid Oxide Electrolysis Cells.

The principle of the CO2 electrolyser is that CO2 (possibly including some CO) is fed to the electrolyser cathode. As current is applied, the CO2 is converted to CO to provide an output stream with a high concentration of CO.

$$2CO2(cathode) \rightarrow 2CO(cathode)+O2(anode)$$

If pure CO2 is inserted into the SOEC the output will be converted CO and unconverted CO2. If needed, the unconverted CO2 can be removed in a CO/CO2 separator operating at temperatures above −100° C. to produce the final high purity CO.

One particular issue with the known gas separator techniques operating at temperatures above −100 C is that they in general are only selective to one or a few molecules and hence have difficulties in removing for example Ar or N2 from the CO+CO2 electrolyser output stream.

Consequently an embodiment of this invention includes:
The use of high purity CO2 as feedstock for the electrolyser
Operating the SOEC electrolyser in schemes where impurities are not added to the product stream even if leakages are present in the electrolyser stack.

Here purity is defined as: Concentration (CO2)+Concentration (CO).

Gas Separation

Four commonly known technologies exist for separating CO2 or CO from a gas stream. These can be characterised as absorption, adsorption, membrane filtering and condensation methods and can all be used for the present invention.

Solvent absorption involves a cyclical process in which CO2 or CO is absorbed from a gas stream directed into a liquid, typically water or an amine. Typically, CO2 is removed and the processed gas stream is then the final purified CO stream. The absorbent liquid can be processed to remove the CO2, which can then be re-used for further electrolysis. The resulting CO2-free liquid is used again for absorption and the process continues. This technique is fairly widely used in a range of applications, but it needs a large amount of power to regenerate the solvent.

Adsorption is based on a cyclical process in which CO2 or CO is adsorbed from a gas stream on to the surface of a solid, typically a mineral zeolite. Typically, CO2 is removed and the processed gas stream is then the final purified CO stream. The solid is then purified in stages using differences in either pressure or temperature to remove the CO2. Common adsorbing technologies are the so-called pressure swing adsorbers (PSA), which are widely used in industry, but may be quite expensive for small scale (<2000 Nm3/h) operation.

Membranes made of polymers or ceramics, can be used to effectively sieve out CO2 or CO from gas streams. The membrane material is specifically designed to preferentially separate the molecules in the mixture. A range of configurations exists either simply as gas separation devices or incorporating liquid absorption stages. This process has not yet been applied on a large scale and there are challenges related to the composition and temperature of the input gases. Furthermore, the selectivity of the membranes is limited and many recycles will typically be needed to obtain high purity (e.g >99.5%) gas output.

Condensation techniques use low temperatures to cool and condense the CO2 from the electrolyser gas streams. Using two coolers where CO2 is condensed at one (e.g. at −90° C.) and CO2 is released from the other (e.g. at −40 C) would allow continuous operation of a condensating CO2 removal unit.

SOEC Based Gas Cleaning.

As an alternative to the above mentioned traditional gas-cleaning techniques, this invention has a dedicated electrolyser design which is used to remove the necessary amount of CO2 from the CO+CO2 stream.

In the following a range of embodiments according to the invention will be described and their advantages will be explained.

Figure 2:
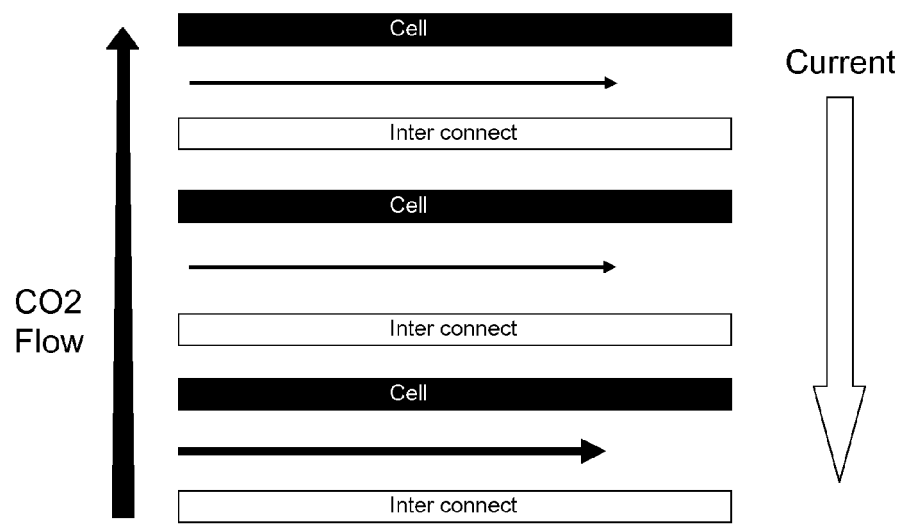

In principle, all CO2 fed to an electrolyser can be converted to CO by applying the correct current and voltage to the cells. Typically, the practical limitation to high conversion ratio is that a stack operates with a single current going through the stack and with slightly non-uniform gas flows between the different cells in the stack. FIG. 2 shows schematically the gas and current flows of a stack. The gas is fed at the bottom and then propagates upwards in the stack to cross the cells. Due to pressure loss in the upward flow channels and inevitable differences in the pressure loss across different cells there will always be some variations in the flows across the different cells.

The current which can be applied to all cells in the stack is limited by the flow across the one cell with the minimum flow, such that the maximum current corresponds to a 100% conversion in the cell with minimum flow. If current is applied which would correspond to a conversion rate above 100% for this minimum flow cell, the current would introduce structural changes in the minimum flow cell and the cell would deteriorate quickly together with the stack. Typically this leads to maximum conversion rates of 80% for 70-cell stacks and 90% for 10-cell stacks.

In one embodiment of the present invention as shown in FIG. 1 it is necessary to separate the CO from the CO2 after the SOEC electrolysis of the input gas of high purity CO2. The CO2 separator can be of any known art as well as a further SOEC as will be disclosed in the following. The separated CO2 can be recycled to the input side of the SOEC electrolyser.

In a further embodiment of the invention a scheme is proposed which allows SOEC stacks to operate with very high conversion rates to directly produce CO output stream of very high purity (e.g. larger than 90% and e.g. larger than 99%). This embodiment is based on the individual control of the current across each cell based on monitoring of the voltage across each cell.

The voltage across an SOEC cell can be expressed as:

$$E = I_{cell}R_{cell} + E_0 + \frac{RT}{2F}\ln\left(\frac{p_{CO2}}{P_{CO}\sqrt{p_{O2}}}\right)$$

where $I_{cell}$ and $R_{cell}$ are the current and resistivity of the relevant cell, respectively. $P_{CO2}$, $p_{CO}$ and $p_{O2}$ are the partial pressures (in bar) of CO2, CO and O2 respectively.

This implies that as the fraction of CO2 in the gas decreases, the voltage across each cell increases quite significantly.

In an embodiment of this invention an SOEC stack is used for direct production of high purity CO. This is done by monitoring the voltage across each cell and individually adjusting the current across each cell to give a desired cell voltage corresponding to a desired level of CO2.

Figure 3:
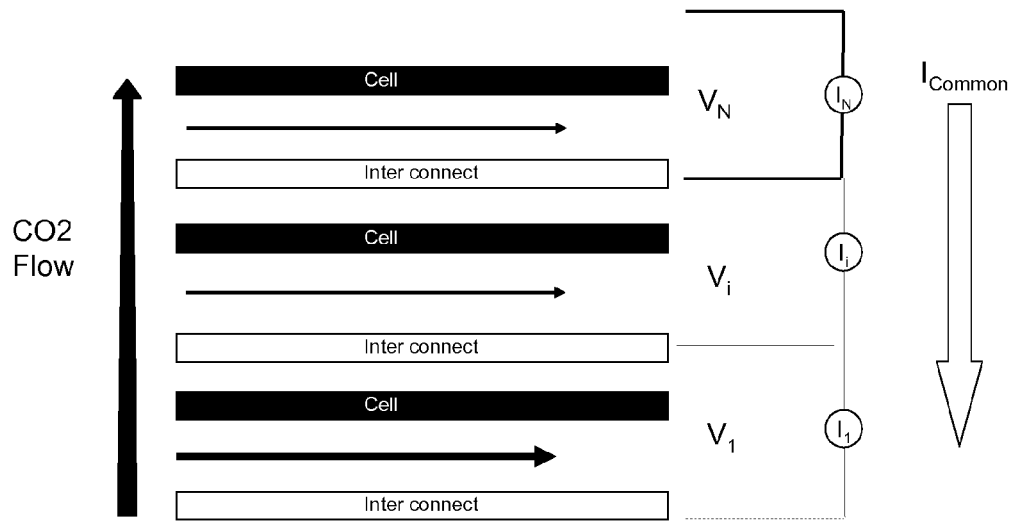

This is shown in FIG. 3, where a stack is fed with a non-uniform flow of CO2 and one common current $I_{Common}$. The current through each cell (e.g. cell 'i') is then adjusted (with the current $\Delta I_i$) to provide a cell specific current (e.g. $I_i=I_{common}+\Delta I_i$) which results in the desired voltage (e.g. $V_{ref}$) and hence CO concentration across the individual cells. This current adjustment scheme can be realised in many ways. This could be by providing a relatively large common current and then removing surplus current with a diode or more flexibly with a transistor and a transistor current controlling circuit. A more energy efficient alternative would be to provide a relatively low common current and then add additional current (e.g. based on switch mode technology) to obtain the desired cell voltage.

Figure 4:
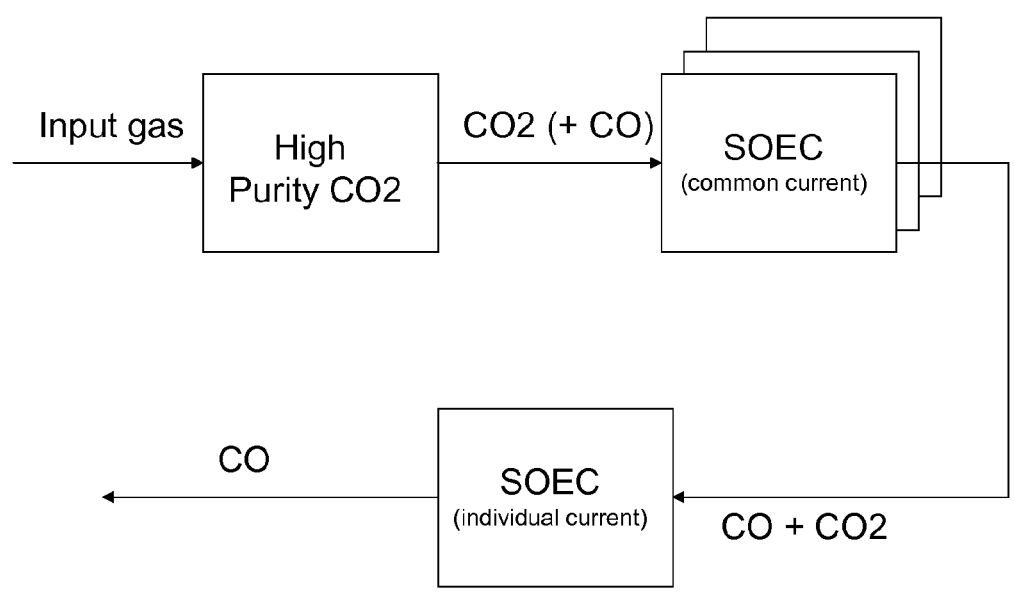

In a further embodiment of this invention as shown in FIG. 4, the individual voltage and current control is only applied to the last stage of the CO2 to CO conversion. The bulk of the CO2 conversion is then performed in traditional stacks where all cells are operating at the same current. This could for example be the conversion of a 100% CO2 stream to 15% CO2 and 85% CO in traditional stack operating solely with common currents for all cells. In a second stage (typically involving fewer cells and higher flows) the 15% CO2 and 85% CO is converted to high purity CO e.g. 99.7% CO and 0.3% CO2 in a stack where current is controlled individually for the different cells or cell groups. This embodiment is cost effective as it provides a relative low cost, traditional SOEC stack for the bulk of the CO2 conversion and the relative more expensive individual voltage and current control SOEC stack for a small part of the conversion.

Avoiding SOEC Stack Related Impurities

To avoid expensive CO2 separation at the output stage of this invention, it is critical that the SOEC electrolyser does not add impurities to the gas stream.

Figure 5:
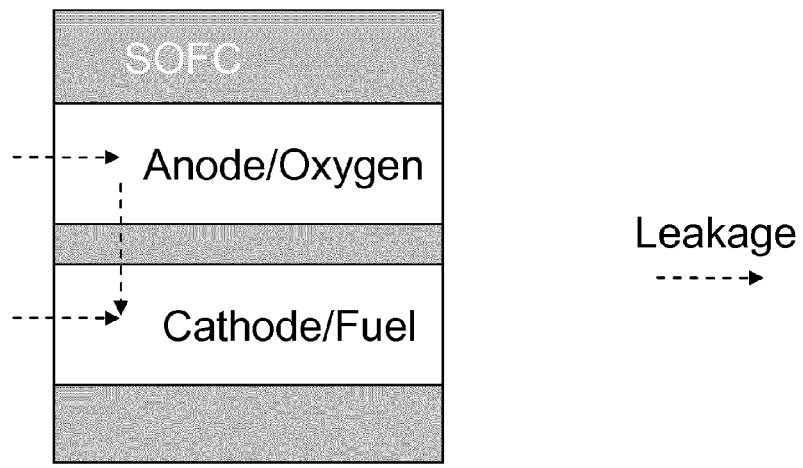

The main source of such potential impurities is leakages in the SOEC stack. This can be leakages between the cathode and the anode side of the stack and it can be leakages between the stack and the external atmosphere as indicated in FIG. 5. These types of leakage are often experienced in Solid Oxide stacks. Leakages are caused partly by imperfect sealings between cells and interconnects and partly because small cracks in solid oxide cell electrolytes may easily exist after production or may evolve during the system lifetime.

If the electrolyser operates with pure oxygen on the anode side, leakages between the anode and the cathode side will not affect the purity of the produced gas (defined as CO2 concentration+CO concentration) as oxygen will combust with CO to form CO2). However, high purity oxygen is very difficult to handle at the high temperatures around 800° C. where it is generated in an SOEC electrolysor. These issues are related to corrosion and possibly even to combustion of the high temperature metal parts. It can therefore be attractive to flush the oxygen side of the electrolysor to reduce the oxygen concentration.

In an embodiment of this invention the oxygen side (the anode) is flushed with CO2 to reduce the oxygen concentration without reducing the CO2+CO purity of the SOEC output gasses even if the SOEC stack is subject to internal leakage.

Figure 6:
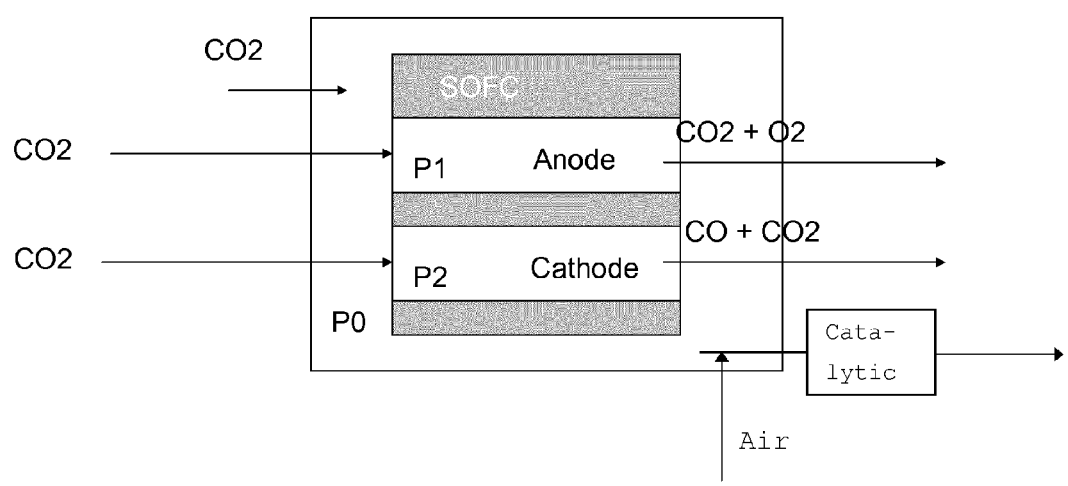

In a further embodiment of this invention as shown in FIG. 6, the SOEC stack or stacks are enclosed in a closed compartment which is flushed with CO2. This implies that the CO2+CO purity of the SOEC output gasses are maintained even if the SOEC stack is subject to external leakage.

In a further embodiment of this invention, different compartments of SOEC stacks are operated at different pressures. If the pressure on the anode (O2) side is P1, the pressure on the cathode (CO2) side is P2 and the pressure outside the stack is P0, then the stack could for example be operated at conditions where:

P0<P1<P2

This will assure that very few impurities penetrates from the external side into the stack and that very few impurities diffuses from the anode side into cathode side, where the CO is produced.

Compartment P0 can further be purged with CO2 where the purge stream after addition of air is passed through a catalytic oxidation step, see FIG. 6. The catalytic oxidation step should comprise a catalyst active in the oxidation reaction between CO and O2.

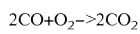

The catalyst could for example be a noble metal catalyst such as Pt and/or Pd optionally combined with $V_2O_5$ and $WO_3$ on an alumina or $TiO_2$ based carrier. The catalyst should operate above 100 C, preferably between 150 and 250 C to assure elimination of CO emitted to the local environment.

In addition, the absolute pressure in compartment denoted P0 can be chosen to be set below atmospheric pressure to assure that CO leaking into P0 cannot escape to the surroundings under any circumstances.

Improving the Purity of the SOEC Input Gas

Figure 10:
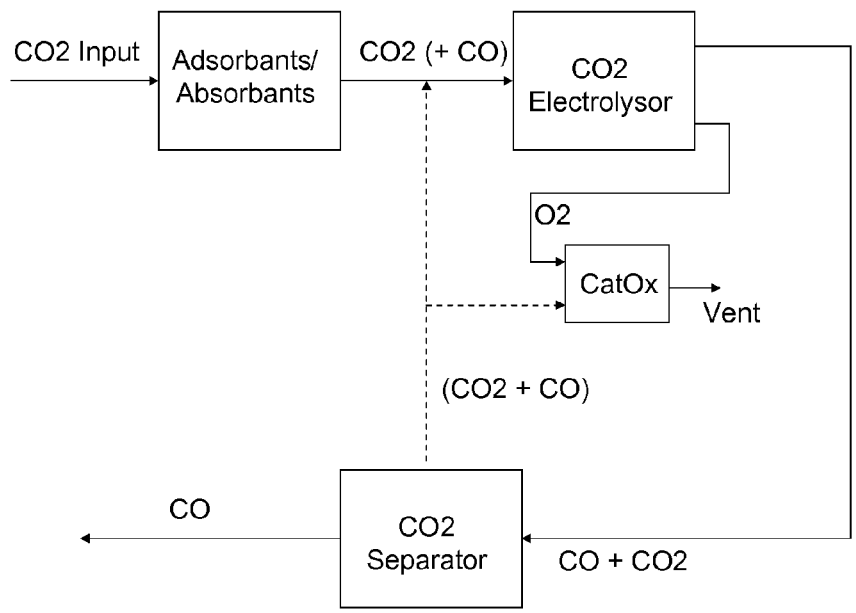

To avoid the use of a very expensive CO2 feedstock, this invention has to take into account that the CO2 feedgas have some contents of undesired "polluting" gasses. This can have two undesirable effects on the system:

The polluting gas may affect the operation of or even poison the SOEC or the CO/CO2 separation equipment For a well designed CO/CO2 separation equipment the polluting gases will in general be separated into the CO2 stream. As it is typically advantageous to recycle this stream to the SOEC, the polluting gases may build up in the system To address these potential issues the present inventions includes embodiments as seen on FIG. 10 where:

Adsorbents or absorbants are used before the SOEC to remove undesired gas contaminations. In particular sulphur species and solixanes are known to poison Solid Oxide cells. These can be absorbed for example with active carbon or Ni- or Cu-based absorbers.

A 'purge' can be build into the recycle stream to avoid the accumulation of polluting gases. However, the recycle stream will typically include CO which in most cases can not be vented safely. One embodiment of this invention includes a purge outlet of the recycle stream which is combined with oxygen from either air or the oxygen output of the SOEC and where the CO and excess O2 forms CO2 on an oxidizing catalyst (CatOx).

Avoiding Carbon Formation and Metal Dusting

One practical issue in relation to high purity CO producing devices operating at elevated temperatures is that carbon may be formed from carbon monoxide through the so-called Boudouard reaction:

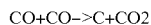

$$CO+CO \rightarrow C+CO_2$$

Deposition of carbon is thermodynamically advantageous in temperature regions below roughly 700° C. and as the CO rich gas cools down carbon may be deposited on for example metal surfaces of pipes or heat exchangers. This may corrode the metal through the mechanism known as metal dusting which eventually may destroy the subjected metal parts. Carbon deposition and metal dusting can be avoided in CO rich environments by using special metals or special coatings of the subjected surfaces. In a special embodiment of this invention, selected metals or coatings are used to avoid carbon formation and metal dusting at the output section of the SOEC electrolyser.

This embodiment includes the use of Ni-rich metals such as Inconel or specifically Inconel 693. This embodiment also includes special coatings of metal surfaces such as surfaces coated with Cu or Sn/Ni coatings for example with 55-65% Sn.

In addition to the coatings mentioned, another possibility is to use a dual tube arrangement. In the case of Cu a viable option is to insert a copper tube inside a tube with the required mechanical strength. Copper tubes loose their mechanical strength at elevated temperatures but by applying a cupper tube inside a for example a high alloy stainless steel tube and assuring intimate contact between the tube surfaces the mechanical strength of the steel tube can be combined with the resistance towards metal dusting of the copper tube. The protection towards metal dusting is due to that the majority of the gas is exposed to the Cu surface. Small portions of gas may find its way to compartments caused by imperfections in the lining but the metal dusting potent gas in these compartments is stagnant and can thus only have an insignificant effect on the metal surface. This is especially advantageous in applications operating close to atmospheric pressures as the forces separating the tubes at a system pressure reduction are directly dependant on the pressure level in the system.

Features of the Invention

1. A device for production of CO with a purity above 90% when the device is provided with CO2 with a purity above 90%, said device comprising at least one Solid Oxide Electrolysis Cell with an anode side and a cathode side and said device further comprises an output gas separation unit, wherein the device is operating at temperatures between 0° C.-50° C., preferably at 10° C.-40°, preferably at room temperature.

2. A device according to claim 1, wherein said device comprises a plurality of Solid Oxide Electrolysis Cells arranged in a stack, and wherein said device further comprises means for individual control of the current across selected Solid Oxide Electrolysis Cells.

3. A device according to claim 2, wherein said individual control of the current is based on monitoring the voltage across selected Solid Oxide Electrolysis Cells.

4. A device according to claim 2 or 3, wherein the output gas separation unit is integrated in said stack.

5. A device according to any of the claims 1 to 3, wherein the output gas separation unit comprises a plurality of cells arranged in a gas separation Solid Oxide Electrolysis Cell stack, and wherein said stack comprises means for individual control of the current across selected cells.

6. A device according to any of the preceding claims, wherein the device further comprises means to flush the anode side of the at least one Solid Oxide Electrolysis Cell with CO2.

7. A device according to any of the preceding claims, wherein the device comprises a compartment enclosing the at least one Solid Oxide Electrolysis Cell, and wherein said compartment comprises means to flush the space enclosed by the compartment.

8. A device according to claim 7, wherein the pressure of the cathode side is higher than the pressure of the anode side, the pressure of the anode side is higher than the pressure of the compartment and the pressure of the compartment is below ambient pressure and wherein the compartment is flushed with $CO_2$ and the $CO_2$ purge is directed from the compartment to a catalytic oxidation reactor utilizing a catalyst comprising a noble metal catalyst such as Pt and or Pd optionally combined with $V_2O_5$ and $WO_3$ on an alumina or $TiO_2$ based carrier and the catalyst operates above 100° C., preferably between 150° C. and 250° C.

9. A device according to any of the preceding claims, wherein said output gas separation unit is one of, a water/amine wash, a Pressure Swing Adsorption or selective membranes.

10. A device according to any of the preceding claims comprising a plurality of stacked Solid Oxide Electrolysis Cells and a plurality of stacks, wherein said stacks are connected in networking connection.

11. A device according to any of the preceding claims, wherein selected components which are subject to metal dusting are made of Ni-rich metals such as Inconel, preferably Inconel 693, or said components are coated with Cu or Sn/Ni coatings, preferably 55-65% Sn.

12. A device according to any of the preceding claims, wherein selected components which are subject to metal dusting are made of double tubes; an inner tube which is a copper tube which is placed inside an outer tube with higher mechanical strength than the copper tube, thereby achieving metal dusting protection and simultaneously combining the mechanical strength of the outer tube with the resistance towards metal dusting of the copper tube.

13. A process for production of high purity CO comprising the steps of
providing a first CO2 gas with a purity above 90% to a device comprising at least one Solid Oxide Electrolysis Cell and comprising a gas separation unit
providing a current to at least one Solid Oxide Electrolysis Cell and producing a second gas comprising CO in said Solid Oxide Electrolysis cell by means of CO2 electrolysis
providing said second gas to the output gas separation unit
operating said gas separation unit at temperatures between 0° C.-50° C., preferably at 10° C.-40°, preferably at room temperature and thereby producing a third output gas comprising CO with a purity above 90%.

14. A process according to claim 13, wherein said device comprises a plurality of Solid Oxide Electrolysis Cells arranged in a stack, and which process further comprises the step of
individually controlling the current across selected Solid Oxide Electrolysis Cells 15. A process according to claim 13 or 14 further comprising the step of
flushing the anode side of the at least one Solid Oxide Electrolysis Cell with CO2.

16. A process according to any of the claims 13-15 further comprising a compartment enclosing the at least one Solid Oxide Electrolysis Cell and further comprising the step of
flushing the space enclosed by said compartment.

17. A process according to claim 16 further comprising the step of
controlling the pressure in the compartment, the anode chambers of the Solid Oxide Electrolysis Cells and the cathode chambers of the Solid Oxide Electrolysis Cells to different levels to reduce diffusion into the cathode chambers.

18. A process according to any of the claims 13-16 wherein the said gas separation comprises the steps
providing said second gas to a gas separation Solid Oxide Electrolysis Cell stack
controlling the current across each individual cell in said gas separation Solid Oxide Electrolysis Cell stack.

19. Process according to any of the claims 13-18 for the production of CO with a purity above 95%, preferably above 99%, preferably above 99.5%.

20. Use of CO as prepared by a device according to any of the claims 1-12 for the production of $CH_3COOH$.

EXAMPLES

Complete System

Figure 7:
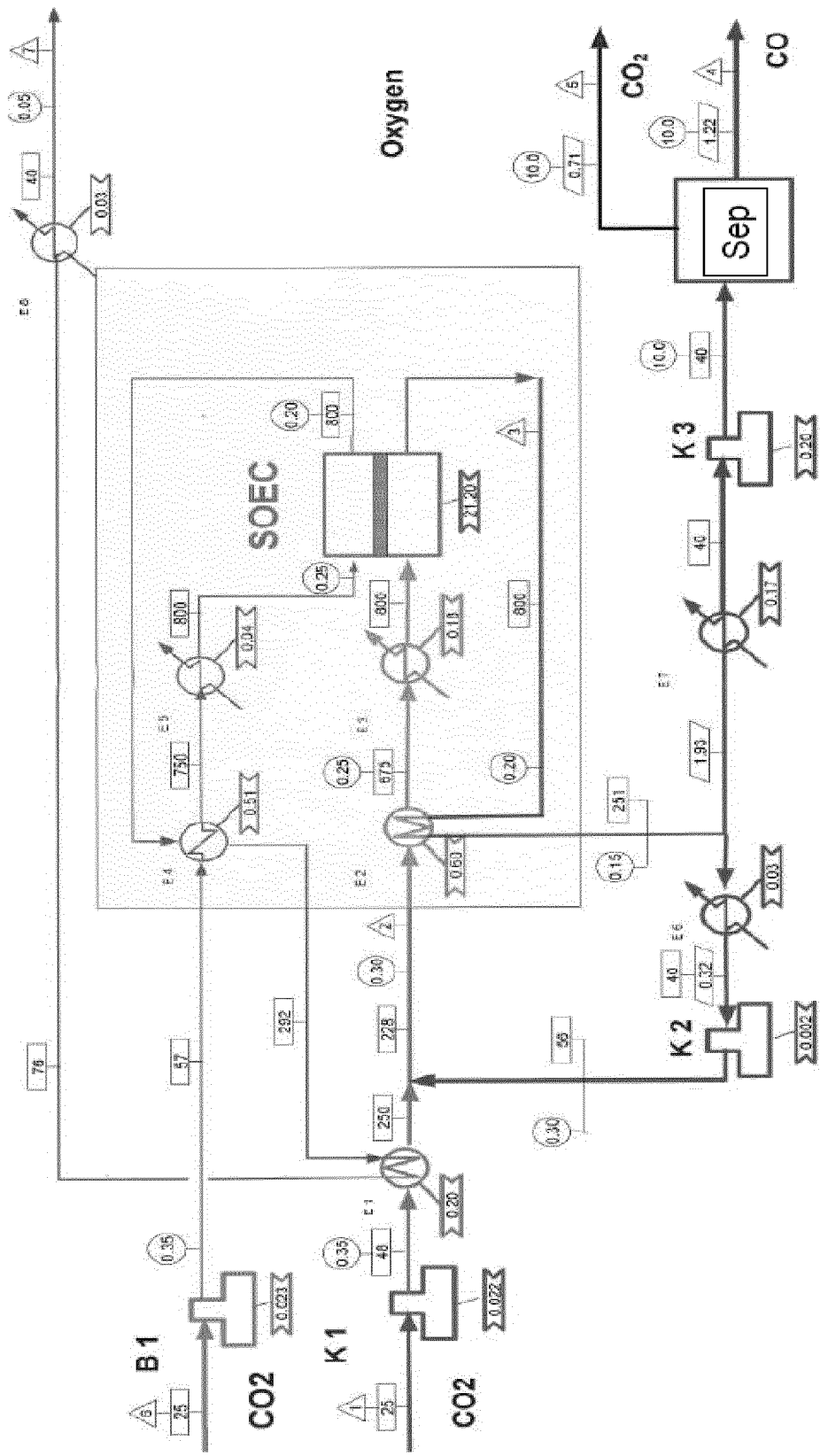

FIG. 7 shows a schematic diagram of one possible embodiment of the invention.

High purity CO2 is flushed to both the 'fuel' and 'oxygen' side of an SOEC stack. To recuperate most of the heat from the system, the input CO2 on the fuel side passes two heat exchangers, while only a single heat exchanger is used on the input side of the 'oxygen' side. The reason for this asymmetric configuration is that oxygen passes from the fuel to the oxygen side and that the heat capacity therefore is highest on the fuel in and oxygen out streams. This is also reflected in the temperatures and duties of the different heat exchangers as shown in FIG. 7.

To avoid metal dusting and carbon formation the heat exchanger at the SOEC fuel side (cathode side) is made of either Ni-rich metals such as Inconel, particularly Inconel 693 or coated metal parts e.g. Sn/Ni coated parts.

With this configuration the output temperatures of the heat exchangers closest to the stacks are 675° C. and 750° C. on the fuel and oxygen side respectively. The SOEC stack is assumed to be operated at the thermo neutral operation point at a temperature of 800° C. Consequently, the input CO2 streams are heated to 800° C. in two electrical heaters. A simple variation of this configuration would be to use one electrical heater at the fuel input, heat the stream here to approximately 825° C. and let the heat exchanging capacity of the SOEC stack heat up the oxygen side input.

In this configuration, the SOEC stack has a capacity to produce approximately 1.2 Nm3/h CO. This could for example be realised with stacks based on 50 cells with an effective area of 10×10 cm. These cells could operate at a current density of the order of 0.75 A/Cm2, a cell voltage of 1.25 V and an effective SOEC conversion efficiency of 3.1 kWh/Nm3.

The SOEC cells could be based on a Ni/YSZ support layer, a Ni/YSZ fuel-side electrode a YSZ electrolyte and an LSM electrode on the Oxygen side.

The CO2 input streams here are chosen to be around 2 Nm3/h at both fuel and oxygen side. This gives a fairly moderate CO concentration of only 63% at the output. This is chosen to allow for a non-uniform flow distribution in the stacks, but much higher output concentrations are possible by using for example individual cell current control.

The 2 Nm3/h input flow to the Oxygen side is chosen to assure an O2 concentration well below 50% at the output. This reduces the speed of corrosion on the oxygen side output and simplifies the choice of materials for heat exchangers and piping.

At the fuel side output, the gas stream is cooled and the majority of the CO is being removed in a separator, which for example could be based on membranes. The remaining CO2 is in this example just send into the air but could also be recycled (including some possible fraction of CO) into the fuel side input. In this configuration a fraction of the SOEC output is recycled to the input, where the residual CO may also help to avoid oxidation at the input of the fuel side of the SOEC stack.

Stack Networking Example

Figure 8:
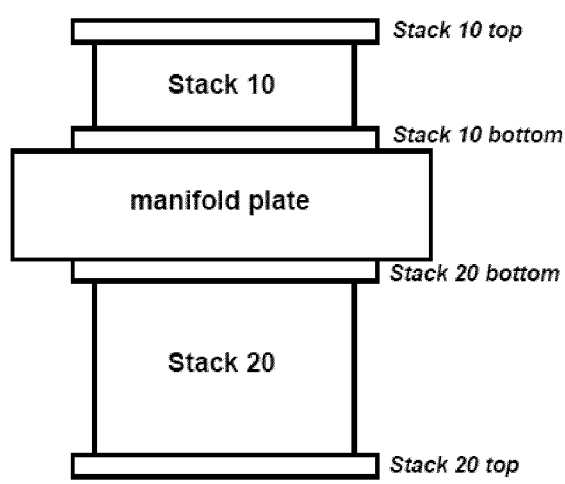

FIG. 8 shows an example of stack networking. The lower stack is made up by 20 cells, the upper one by 10 cells. The bottom of both stacks is in this case facing the internal manifold plate.

Avoiding Contaminations from SOEC Stack Leakages

Figure 9:
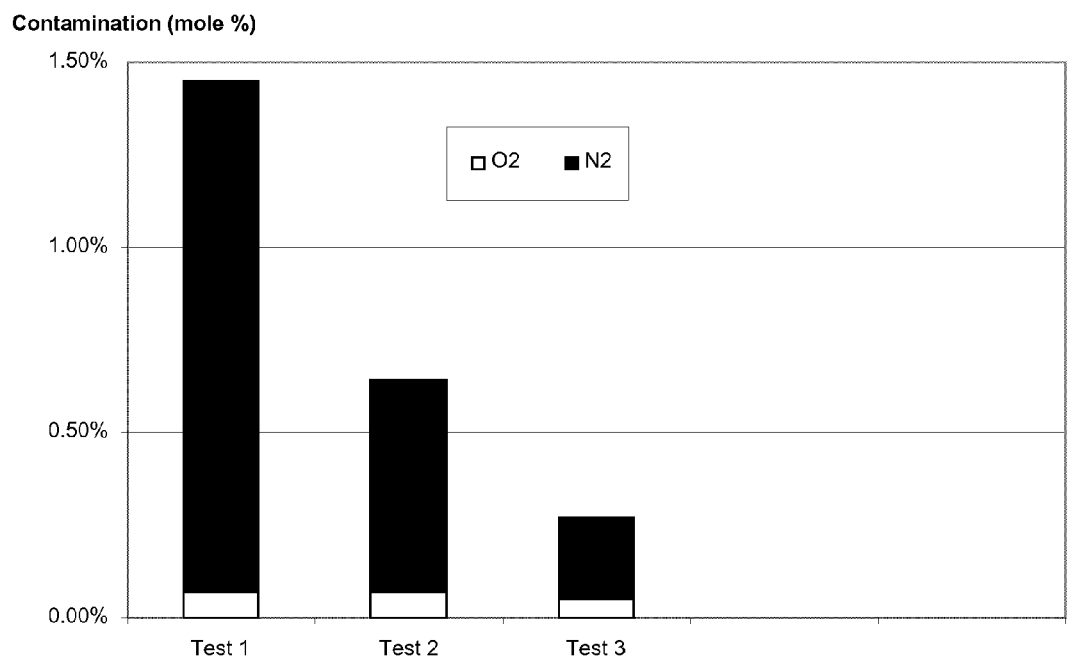

FIG. 9 shows the importance of actively handling the possible impurities introduced in the output stream of an SOEC system by stack leakages.

Test 1 shows the impurities (N2 and O2) of a stack operating with uniform pressure and with air used for flushing the oxygen side.

In test 2 CO2 was used instead of air to flush the oxygen side and in this case the impurity level have been reduced from roughly 1.5 mole % to less than 0.75 mole %.

In test 3, the pressure of the fuel side (the cathode) has been increased to be roughly 100 mbar higher than on the oxygen side and in the external stack compartment. CO2 was used for flushing the oxygen side. In this test the impurity level was below 0.3 mole % which is sufficient for meeting for example the standard industrial grade for bottled CO.

The invention claimed is:

1. A process for production of high purity CO, comprising the steps of:
   providing a first $CO_2$ gas with a purity above 90% to a device comprising at least one Solid Oxide Electrolysis Cell and comprising a gas separation unit;
   providing a current to at least one Solid Oxide Electrolysis Cell and producing a second gas comprising CO in said Solid Oxide Electrolysis cell by means of $CO_2$ electrolysis providing said second gas to the output gas separation unit; and
   operating said gas separation unit at temperatures between 0° C.-50° C., and thereby producing a third output gas comprising CO with a purity above 90%.

2. A process according to claim 1, wherein said device comprises a plurality of Solid Oxide Electrolysis Cells arranged in a stack, and which process further comprises the step of individually controlling the current across selected Solid Oxide Electrolysis Cells.

3. A process according to claim 1 further comprising the step of flushing the anode side of the at least one Solid Oxide Electrolysis Cell with $CO_2$.

4. A process according to claim 1 further comprising a compartment enclosing the at least one Solid Oxide Electrolysis Cell and further comprising the step of flushing the space enclosed by said compartment.

5. A process according to claim 4 further comprising the step of controlling the pressure in the compartment, the anode chambers of the Solid Oxide Electrolysis Cells and the cathode chambers of the Solid Oxide Electrolysis Cells to different levels to reduce diffusion into the cathode chambers.

6. A process according to claim 1 wherein the said gas separation comprises the steps of:
   providing said second gas to a gas separation Solid Oxide Electrolysis Cell stack; and
   controlling the current across each individual cell in said gas separation Solid Oxide Electrolysis Cell stack.

7. A process according to claim 1 for the production of CO with a purity above 95%.

* * * * *